United States Patent [19]

Ripke

[11] Patent Number: 5,478,931
[45] Date of Patent: Dec. 26, 1995

[54] METHOD OF NEUTRALIZING ALKYL POLYGLYCOSIDE SOLUTIONS

[75] Inventor: Norbert Ripke, Haltern, Germany

[73] Assignee: Huels Aktiengesellschaft, Marl, Germany

[21] Appl. No.: 150,789

[22] Filed: Nov. 12, 1993

Related U.S. Application Data

[63] Continuation of Ser. No. 904,265, Jun. 25, 1992, abandoned.

[30] Foreign Application Priority Data

Jul. 4, 1991 [DE] Germany .......................... 41 22 071.4

[51] Int. Cl.$^6$ .............................. C07G 17/00; C07H 5/04; G01N 35/08; G01N 35/00
[52] U.S. Cl. .......................... 536/124; 536/18.6; 436/52; 436/43
[58] Field of Search .................... 536/124, 1.1, 123.1, 536/18.6, 127, 18.4; 568/852; 564/269; 436/52, 43

[56] References Cited

U.S. PATENT DOCUMENTS

| | | | |
|---|---|---|---|
| H619 | 4/1989 | McDaniel, Jr. et al. | 536/18.6 |
| 3,839,318 | 10/1974 | Mansfield | 536/18.6 |
| 4,393,203 | 7/1983 | Mao et al. | 536/18.4 |
| 4,713,447 | 12/1987 | Letton | 536/18.6 |

*Primary Examiner*—Michael G. Wityshyn
*Assistant Examiner*—Louise N. Leary
*Attorney, Agent, or Firm*—Oblon, Spivak, McClelland, Maier & Neustadt

[57] ABSTRACT

The final mixture in the manufacture of alkyl polyglycosides comprises an acidic, non-aqueous solution of alkyl polyglycosides in long chain alcohols. The invention relates to a novel method of neutralizing these solutions. First, a small part of the solution is withdrawn and a mixture comprised of an alcohol or alcohol mixture having 1–6 C atoms and water is added thereto, the withdrawn part is neutralized with an aqueous-, alcoholic-, or aqueous-alcoholic alkali. The amount of alkali necessary to neutralize the alkyl polyglycoside solution is calculated and added to the alkyl polyglycoside solution.

11 Claims, No Drawings

METHOD OF NEUTRALIZING ALKYL POLYGLYCOSIDE SOLUTIONS

This application is a continuation of Ser. No. 07/904,265, filed on Jun. 25, 1992, now abandoned.

BACKGROUND OF THE INVENTION

1. Field of the Invention

The invention relates to a method of neutralizing acid solutions of alkyl polyglycosides having alkyl groups with 8–24 C atoms in alcohols having 8–24 C atoms.

2. Discussion of the Background

Alkyl polyglycosides are nontoxic and readily degradable surfactants. Accordingly, they are used as detergents and cleaning agents, and also as emulsifiers and dispersants. However, they only have the desired interfacial properties if the alkyl groups contain at least 8 C atoms.

Alkyl glycosides and alkyl polyglycosides with long chain alkyl groups are generally manufactured by multi-step syntheses. EP-A-0 306 652 discloses a two-stage method in which an n-butylglycoside is produced by glycosidation of n-butanol, and then the desired long chain alkyl polyglycoside is produced by transglycosidation with a long chain alcohol. Both glycosidation and transglycosidation reactions are catalyzed by acids. After completion of the transglycosidation, the mixture is neutralized, and the excess long chain alcohol is distilled off.

Single-step reactions for manufacturing alkyl polysaccharides are known. U.S. Pat. No. 3,839,318 discloses a process for directly reacting saccharides with long chain alcohols, under special reaction conditions. The mixture must be neutralized after completion of the reaction, and the excess long chain alcohol is subsequently distilled off.

EP-A-0 249 013 recognizes that the degree of polymerization of alkyl polyglycosides can be influenced during transglycosidation by the amount of acid added. Here the mixture is neutralized after completion of the transglycosidation. Sodium hydroxide is used in an amount equivalent to the amount of sulfuric acid used. However, this technique is too imprecise for accurate adjustment to a desired pH value. For example, it does not take into account losses of acid which can occur by esterification.

Because saccharides readily thermally decompose in acid medium, the acid present prior to the distillation-off of the excess alcohols must be neutralized at least to a major extent. Such neutralization presents a problem, because it is not possible to directly measure the pH value of a fatty alcohol solution.

SUMMARY OF THE INVENTION

Accordingly, one object of this invention is to provide a method whereby acid solutions of alkyl polyglycosides in long chain alcohols can be quickly and accurately neutralized and adjusted to a specified pH.

Surprisingly, this object, and other objects which will become obvious from a description of the invention provided hereinafter, have been satisfied with the discovery of the present method of neutralizing an acid solution of alkyl polyglycosides having alkyl groups with 8–24 C atoms in alcohols having 8–24 C atoms comprising withdrawing a small part of the solution and adding thereto 2–10 quantities of an alcohol/water mixture containing 50–90 wt. % alcohol or alcohol mixture having 1–6 C atoms and 50–10 wt. % water, and then neutralizing said withdrawn part with aqueous-, alcoholic-, or aqueous-alcoholic alkali.

DETAILED DESCRIPTION OF THE INVENTION

Here the term "neutralization" does not necessarily mean that a pH of 7 is established. In the sense intended by the present invention, "neutralization" means that the acid present is neutralized at least to a substantial degree. There may be overtitration, so that the result is a weakly alkaline solution. The neutralizations carried out may thus lead to pH values of 6.5–11, preferably 7–10.

The term "a small part" should be understood to mean a portion up to about 20%. In general it entirely suffices if one chooses an amount of alkali required to neutralize 0.1–5% of the solution.

The inventive method is preferably employed with continuously fed alkyl polyglycoside solutions. Under such conditions, a side stream is taken off. One determines the amount of alkali required for a given pH, and then the main stream is treated with a calculated amount of alkali.

In general, 10–60% solutions, preferably 15–35% solutions, of alkyl polyglycosides are employed.

The sugar moiety in the alkyl polyglycosides may be derived from a monosaccharide such as glucose, mannose, gulose, galactose, and talose, or from a di- or oligosaccharide. The saccharides may have 1,2-, 1,3-, 1,4-, or 1,6-linkages. Alpha- or beta-linkages may be present. The chains may be linear or branched. The mean degree of polymerization is generally in the range 1–10. The sugar moiety is preferably derived from glucose.

The alkyl groups of the alkyl polyglycosides are generally the same as those of the alcohols in which the alkyl polyglycosides are dissolved.

Suitable alcohols with 8–24 C atoms are, for example, octanol, nonanol, decanol, 10-undecen-1-ol, dodecanol, tetradecanol, and stearyl alcohol. The alcohols may be linear or may contain branches. Natural or synthetic alcohols or mixtures of alcohols may be used.

The alkyl groups of the alkyl polyglycosides and the alcohols used as solvents preferably have carbon chains with 10–18 C atoms.

The solutions of the alkyl polyglycosides also contain the acid catalysts required for transglycosidation or for glycosidation in the case of single-step manufacturing methods. Examples of catalysts include a mineral acid, such as sulfuric acid or phosphoric acid, and an organic acid such as aryl-, alkyl-, and aralkylsulfonic acid. The acid numbers of these solutions generally lie in the range 1–10 mg KOH/g, preferably 1.5–5 mg KOH/g.

The alcohol/water mixture employed preferably contains 60–80 wt. % alcohol or alcohol mixture and 40–20 wt. % water. Alcohols suitable for this mixture include methanol, ethanol, n-propanol, isopropanol, n-butanol, isobutanol, n-pentanol, and n-hexanol. Alcohols with 2–4 C atoms are preferred.

Examples of alkali or alkalies to be added in the neutralization step include ammonia, amines, alkali hydroxides, and alkaline earth hydroxides. Preferably, alkali hydroxides such as sodium hydroxide and potassium hydroxide are used.

The neutralizations of the side solution and the main solution are generally carried out at 20°–90° C.

The amount of alkali required for the neutralization step may be determined within a few seconds. The time from the addition of the alcohol/water mixture to the addition of alkali to the main solution ranges from only 30 seconds to 2 minutes. The method is so rapid that it tan be employed successfully "on stream" in a continuous process. A signal produced in the neutralization in the side stream can be forwarded directly to the main stream, where the quantity of alkali is accurately added. This method results in savings of time and improved yields per unit space per unit time.

Examples of mixtures prepared employing a side stream or a withdrawn part of the alkyl polyglycoside solutions are given in Table 1.

TABLE 1

| Mixture | a | b | c | d |
|---|---|---|---|---|
| Alkyl polyglycoside solution (25% solution in dodecanol, with the alkyl group being dodecyl, and the sugar moiety being glucose) | 10 | 10 | 10 | 10 |
| N-Butanol | | 30 | 30 | 50 | — |
| Isopropanol | — | — | — | 30 |
| Water | 10 | 12 | 30 | 20 |

The titration curve for the neutralization of these solutions with aqueous 0.1 N NaOH is steep in the equivalence region, so that the quantities of NaOH needed for a desired pH can be accurately determined.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of neutralizing a continuous stream of acid solution of alkyl polyglycosides having alkyl groups with 8–24 C atoms in alcohols having 8–24 C atoms to a pH of 7–10, comprising withdrawing a side stream of up to about 20% of the continuous stream and adding thereto 2–10 times the amount withdrawn of a mixture of 50–90 wt. % alcohol or alcohol mixture having 1–6 C atoms and 50–10 wt. % water, then neutralizing said withdrawn side stream with an alkali selected for the group consisting of aqueous alkali, alcohol alkali, and aqueous-alcohol alkali, calculating the amount of alkali necessary to neutralize the continuous stream of alkyl polyglycoside solution based upon the amount of alkali required to neutralize the withdrawn side stream, and continuously adding the calculated amount of alkali to the continuous stream of alkyl polyglycoside solution.

2. The method according to claim 1, wherein a mixture of 60–80 wt. % alcohol or alcohol mixture and 40–20 wt. % water is added to the withdrawn alkyl polyglycoside.

3. The method according to claim 1, wherein the alcohol in the added mixture has 2–4 C atoms.

4. The method according to claim 1, wherein the time from the addition of the alcohol/water mixture to the addition of calculated alkali ranges from 30 seconds to 2 minutes.

5. The method according to claim 1, wherein the alkyl group of the alkyl polyglycoside contains 10–18 C atoms.

6. The method according to claim 1, wherein the alcohol used as a solvent in the acid solution of alkyl polyglycosides contains 10–18 C atoms.

7. The method according to claim 1, wherein 0.1–5% of the acid solution of alkyl polyglycosides is withdrawn.

8. The method according to claim 1, wherein the neutralization of the withdrawn part is carried out at 20°–90° C.

9. The method according to claim 1, wherein the neutralization of the alkyl polyglycoside solution is carried out at 20°–90° C.

10. The method according to claim 1, wherein the alkali is selected from the group consisting of ammonia, amines, alkali hydroxides, alkaline earth hydroxides, and mixtures thereof.

11. The method according to claim 10, wherein the alkali hydroxide is selected from the group consisting of sodium hydroxide and potassium hydroxide.

* * * * *